United States Patent
Salla et al.

(10) Patent No.: US 7,844,317 B2
(45) Date of Patent: Nov. 30, 2010

(54) METHOD AND SYSTEM FOR ESTIMATING THREE-DIMENSIONAL RESPIRATORY MOTION

(75) Inventors: Prathyusha K. Salla, Waukesha, WI (US); Gopal B. Avinash, New Berlin, WI (US); Jason A. Polzin, Lake Mills, WI (US)

(73) Assignee: General Electric Company, Schenectady, NY (US)

( * ) Notice: Subject to any disclaimer, the term of this patent is extended or adjusted under 35 U.S.C. 154(b) by 1867 days.

(21) Appl. No.: 10/723,728

(22) Filed: Nov. 26, 2003

(65) Prior Publication Data

US 2005/0113671 A1 May 26, 2005

(51) Int. Cl.
*A61B 5/05* (2006.01)
(52) U.S. Cl. .................. 600/407; 600/448; 600/437; 600/410; 600/428; 382/128
(58) Field of Classification Search ................ 600/410, 600/407, 415, 424, 437, 441–443, 463, 428, 600/448, 413; 378/8, 111; 382/294, 128, 382/285; 348/169
See application file for complete search history.

(56) References Cited

U.S. PATENT DOCUMENTS

| | | | |
|---|---|---|---|
| 4,712,560 A | | 12/1987 | Schaefer et al. |
| 4,961,426 A | | 10/1990 | Spraggins et al. |
| 4,994,965 A | | 2/1991 | Crawford et al. |
| 5,353,354 A | * | 10/1994 | Keller et al. ............. 382/128 |
| 5,363,844 A | | 11/1994 | Riederer et al. |
| 5,477,144 A | | 12/1995 | Rogers, Jr. |
| 5,701,897 A | | 12/1997 | Sano |
| 5,810,729 A | * | 9/1998 | Hushek et al. ............. 600/410 |
| 5,899,861 A | * | 5/1999 | Friemel et al. ............ 600/443 |
| 5,997,883 A | | 12/1999 | Epstein et al. |
| 6,014,473 A | * | 1/2000 | Hossack et al. ............ 382/294 |

(Continued)

OTHER PUBLICATIONS

Daniel, F. Leotta et al, Three-Dimensional Ultrasound Imaging Using Multiple Magnetic Tracking Sensors and Miniature Magnetic Sensors, 1995, IEEE Ultrasonics Symposium, 1415-1418.*

(Continued)

*Primary Examiner*—Brian Casler
*Assistant Examiner*—Joel M Lamprecht
(74) *Attorney, Agent, or Firm*—Fletcher Yoder

(57) ABSTRACT

One or more techniques are provided for measuring the motion of an organ in three dimensions. As provided by the technique, the motion of the organ along each dimension may be determined by a suitable methodology. Where sensor-based motion measurements are suitable, one or more sensors may be placed on a patient to measure internal motion of the organ of interest along one or more perpendicular axes. Where image-based techniques are suitable, the motion of the internal organ along a perpendicular axis may determined using pre-acquisition image data or acquisition image data when suitable. Concurrent motion vectors for all three dimensions may be obtained from the motion data acquired for the perpendicular axes by the disparate methodologies. The concurrent motion vectors may be combined to describe the three-dimensional motion of the organ over time. Validation of the motion data may be performed for each of the one-dimensional motion data sets using motion data acquired by image-based methods, or other image-based methods, for a respective axis.

42 Claims, 5 Drawing Sheets

U.S. PATENT DOCUMENTS

| | | | |
|---|---|---|---|
| 6,144,874 A | 11/2000 | Du | |
| 6,144,875 A | 11/2000 | Schweikard et al. | |
| 6,233,478 B1 | 5/2001 | Liu | |
| 6,278,890 B1* | 8/2001 | Chassaing et al. | 600/407 |
| 6,295,464 B1* | 9/2001 | Metaxas | 600/407 |
| 6,298,260 B1 | 10/2001 | Sontag et al. | |
| 6,324,254 B1 | 11/2001 | Pflaum | |
| 6,358,208 B1 | 3/2002 | Lang et al. | |
| 6,690,963 B2* | 2/2004 | Ben-Haim et al. | 600/424 |
| 6,694,166 B2* | 2/2004 | Salome et al. | 600/410 |
| 6,791,323 B2 | 9/2004 | Wang et al. | |
| 6,836,529 B2 | 12/2004 | Li et al. | |
| 7,529,431 B2* | 5/2009 | Bayer et al. | 382/285 |
| 7,597,665 B2* | 10/2009 | Wilk et al. | 600/459 |
| 2001/0031919 A1* | 10/2001 | Strommer et al. | 600/424 |
| 2002/0026115 A1* | 2/2002 | Nehrke et al. | 600/410 |
| 2002/0065455 A1* | 5/2002 | Ben-Haim et al. | 600/407 |
| 2002/0091314 A1 | 7/2002 | Schlossbauer et al. | |
| 2002/0156371 A1 | 10/2002 | Hedlund et al. | |
| 2002/0165446 A1* | 11/2002 | Ryf et al. | 600/410 |
| 2003/0188757 A1 | 10/2003 | Yanof et al. | |
| 2004/0006266 A1 | 1/2004 | Ustuner et al. | |
| 2004/0102695 A1 | 5/2004 | Stergiopoulos et al. | |
| 2004/0155653 A1 | 8/2004 | Larson et al. | |
| 2004/0260346 A1 | 12/2004 | Overall et al. | |

OTHER PUBLICATIONS

Huesman RH, GJ Klein, BW Reutter, and TF Budinger. Preliminary studies of cardiac motion in positron emission tomography. Report LBNL-41433, Lawrence Berkeley National Laboratory. Mar. 2001.

Keegan, Jennifer, et al., Subject Specific Motion Correction Factors for Magnetic Resonance Coronary Angiography, International Workshop on Medical Imaging and Augmented Reality, pp. 67-71. 2001.

Bohning, Daryl E., et al., PC-Based System for Retrospective Cardiac and Respiratory Gating of NMR Data, Magnetic Resonance in Medicine (16), pp. 303-316. 1990.

Yuan, Qing, et al., Cardiac-Respiratory Gating Method for Magnetic Resonance Imaging of the Heart, Magnetic Resonance in Medicine (43), pp. 314-318. 2000.

* cited by examiner

METHOD AND SYSTEM FOR ESTIMATING THREE-DIMENSIONAL RESPIRATORY MOTION

BACKGROUND OF THE INVENTION

The present technique relates generally to the measurement of motion in medical imaging. More specifically, the present technique relates to the use of sensors and/or image data to measure the three-dimensional motion of an organ.

In the medical field, it is often desirable to generate images of the internal organs or structure of a patient for diagnosis or examination. For example, magnetic resonance imaging (MRI) and computed tomography (CT) are two well known examples of imaging modalities used to generate images of the internal organs or structures of a patient. The reconstructed images, however, may be flawed or contain artifacts due to the motion of internal organs, such as the heart, lungs, diaphragm, stomach, and so forth. In particular, if the imaged region has undergone motion during the imaging process, various motion-related artifacts or discontinuities may be present in the reconstructed image.

For example, images acquired of one or more organs in the torso of a patient, such as the heart, lungs, stomach, and so forth, may have motion-related artifacts associated with cardiac and/or respiratory activity. One problem that may arise in attempting to estimate the motion of an imaged organ is that the various techniques employed may not provide sufficient motion information in all of the dimensions of interest.

For example, sensors that measure mechanical motion or some characteristic of motion may be situated on the patient. Such sensors may measure a variety of parameters, such as displacement, pressure, velocity, acceleration, and so forth, which may be processed to characterize the internal motion of one or more organs. However the motion characterization derived from such an external sensors or sensors is typically one-dimensional, i.e., motion is only described along a single axis spanning the sensor and the organ. Due to the shape of the human body, however, it is typically difficult to situate three mechanical sensors sufficiently near to an organ of interest such that the sensors are orthogonal to one another. The three-dimensional motion of the organ, therefore, cannot be easily described using mechanical sensors.

Similarly, image data, such as pre-acquisition data in the form of a Navigator Echo generated by an MRI system, may be used to measure organ motion. Such techniques, however, require anatomical landmarks that can be easily distinguished and used to gauge motion. Such landmarks are generally not available along all three-dimensions for most organs of interest. As a result, pre-acquisition image techniques may also be essentially one-dimensional in characterizing motion. At the very least, such techniques are not generally useful for characterizing the motion of an organ in three-dimensions. The absence of reliable data describing the three-dimensional motion of an imaged organ may impair efforts to reduce or eliminate motion-related artifacts in the image data. It is, therefore, desirable to develop a technique for reliably estimating the motion of an imaged organ in three-dimensions with good temporal resolution.

BRIEF DESCRIPTION OF THE INVENTION

The present invention is directed to a technique for determining the three-dimensional motion of an organ. In general, the technique utilizes one or more methodologies to determine motion such that motion along the three-dimensional axes of an object is measured by one or more methodologies. For example, sensor-based measurement may be used to measure motion, such as along one or two perpendicular axes relative to the organ. Image-based motion measurement techniques, using pre-acquisition or acquisition image data, may also be used to measure motion along one or more perpendicular axes. The measured motion along each perpendicular axis may be used to derive concurrent motion vectors for the organ for all three dimensions over time.

In accordance with one aspect of the present technique, a method for determining the motion of an organ is provided. In the present technique, a first set of one-dimensional motion data for an organ may be acquired along a first axis by a first methodology. A second set of one-dimensional motion data for the organ may be acquired along a second axis by a second methodology. A third set of one-dimensional motion data for the organ may be acquired along a third axis by a third methodology. The three axes are perpendicular to one another. One or more concurrent motion vectors may be derived from each of the first, second, and third sets of one-dimensional motion data. The one or more concurrent motion vectors may be combined to generate a set of three-dimensional motion data for the organ. Systems and computer programs that afford functionality of the type defined by this method are also provided by the present technique.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

In the field of medical imaging, the motion of an organ may lead to motion artifacts in images of the organ. Various techniques may be employed to estimate the motion of the imaged organ, allowing image acquisition and/or image processing to be adapted to reduce motion artifacts, such as by using gating or motion correction techniques. In the present technique, multiple sources of motion data may be employed to characterize the three-dimensional motion of an organ or organs being imaged.

Figure 1:
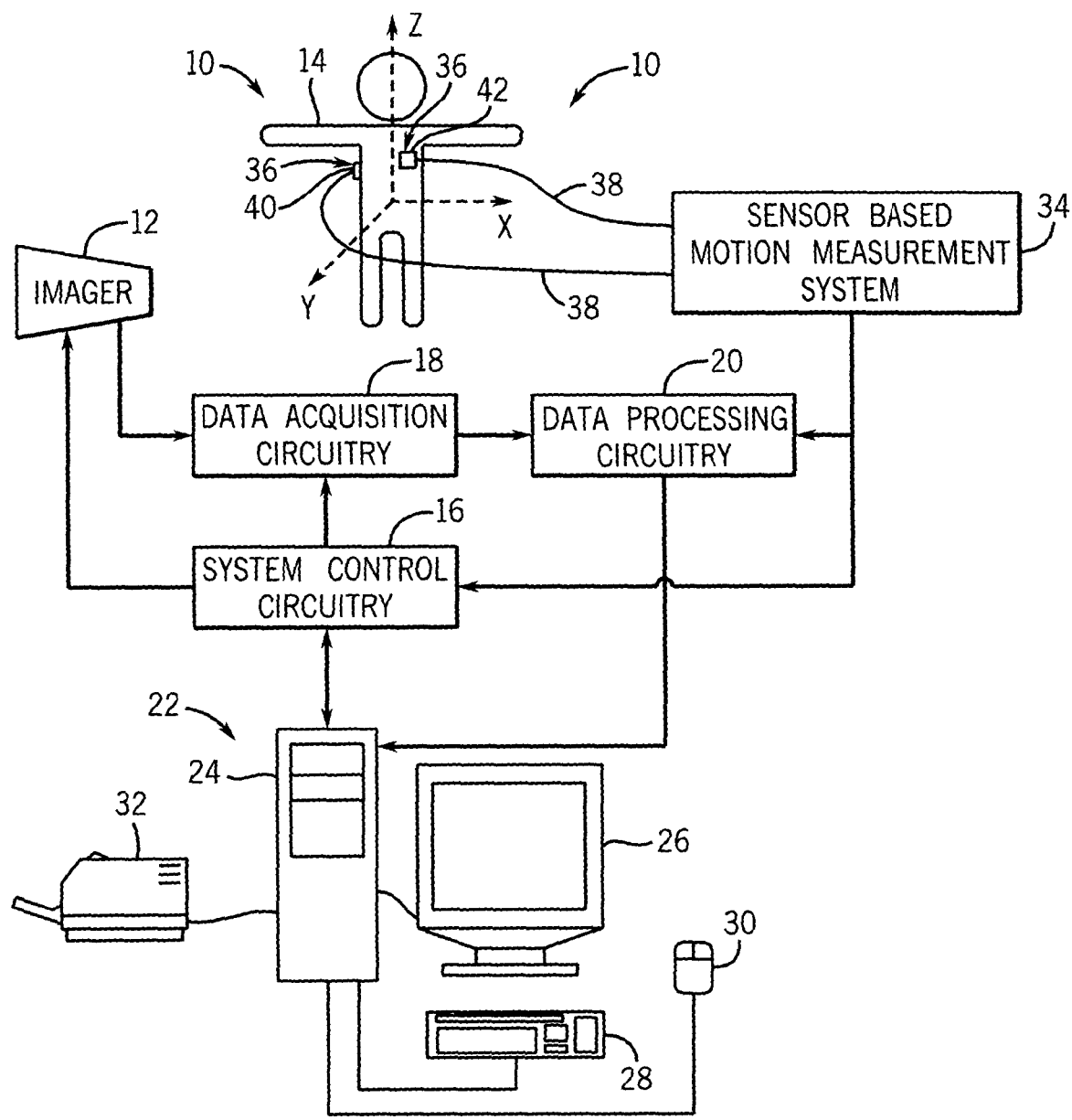
FIG. 1 is a general diagrammatical representation of certain functional components of an exemplary generic imaging system capable of gating via the present technique.

An exemplary imaging system 10 capable of operating in accordance with the present technique is depicted in FIG. 1. Generally, the imaging system 10 includes some type of imager 12 that detects signals and converts the signals to useful data. As described more fully below, the imager 12 may operate in accordance with various physical principals for creating the image data. In general, however, the imager 12 creates image data indicative of the region of interest in a patient 14, either in a conventional support, such as photographic film, or in a digital medium.

The imager 12 operates under the control of system control circuitry 16. The system control circuitry 16 may include a wide range of circuits, such as radiation source control circuits, timing circuits, circuits for coordinating data acquisition in conjunction with patient or table movements, circuits for controlling the position of radiation sources and detectors, and so forth. In the present context, the system control circuitry 16 may also include memory elements, such as magnetic or optical storage media, for storing programs and routines executed by the system control circuitry 16 or by associated components of the system 10. The stored programs or routines may include programs or routines for performing all or part of the present technique.

Image data or signals acquired by the imager 12 may be processed by the imager 12, such as for conversion to digital values, and provided to data acquisition circuitry 18. The data acquisition circuitry 18 may perform a wide range of processing functions, such as adjustment of digital dynamic ranges, smoothing or sharpening of data, as well as compiling of data streams and files, where desired. In situations where pre-acquisition image data, such as Navigator pulses in magnetic resonance imaging (MRI), are acquired, the data acquisition circuitry 18 may provide image data to the system control circuitry 16 for prospective gating or other processing.

The data acquisition circuitry 18 may also transfer acquisition image data to data processing circuitry 20, where additional processing and analysis are performed. The data processing circuitry 20 may perform substantial analyses of image data, including ordering, sharpening, smoothing, feature recognition, and so forth. In addition, the data processing circuitry 20 may receive motion data for one or more organs from one or more sensor-based motion detection systems 34, as discussed in detail below. Based on image-based and/or sensor-based motion data, respiration gating may be facilitated by the data processing circuitry 20, such as by determining motion attributes, motion thresholds, and/or gating intervals that may be provided to the system control circuitry 16 and/or operator workstation 22. The processed image data may be stored in short or long term storage devices, such as picture archiving communication systems, which may be located within or remote from the imaging system 10 and/or reconstructed and displayed for an operator, such as at the operator workstation 22.

In addition to displaying the reconstructed image, the operator workstation 22 may control the above-described operations and functions of the imaging system 10, typically via an interface with the system control circuitry 16. The operator workstation 22 may include one or more processor-based components, such as general purpose or application specific computers 24. In addition to the processor-based components, the operator workstation 22 may include various memory and/or storage components including magnetic and optical mass storage devices, internal memory, such as RAM chips. The memory and/or storage components may be used for storing programs and routines for performing the techniques described herein that are executed by the operator workstation 22 or by associated components of the system 10. Alternatively, the programs and routines may be stored on a computer accessible storage and/or memory remote from the operator workstation 22 but accessible by network and/or communication interfaces present on the operator workstation 22.

The operator workstation may also comprise various input/output (I/O) interfaces, as well as various network or communication interfaces. The various I/O interfaces may allow communication with user interface devices, such as a display 26, keyboard 28, mouse 30, and printer 32, that may be used for viewing and inputting configuration information and/or for operating the imaging system 10. The various network and communication interfaces may allow connection to both local and wide area intranets and storage networks as well as the Internet. Though the various I/O and communication interfaces are indicated as operating through wires or lines in FIG. 1, it is to be understood that wireless interfaces may also be utilized where appropriate.

As one of ordinary skill in the art will appreciate, more than a single operator workstation 22 may be provided for an imaging system 10. For example, an imaging scanner or station may include an operator workstation 22 which permits regulation of the parameters involved in the image data acquisition procedure, whereas a different operator workstation 22 may be provided for manipulating, enhancing, and viewing results and reconstructed images.

The motion of the lungs or other organs of interest, such as the diaphragm or heart, may be measured in a variety of ways. In some cases, the motion data of interest may be derived using data obtained from the image scanner 12 itself. Alternatively, sensor-based motion determination techniques may be employed in conjunction with or instead of data-based techniques which rely on the imager 12. In these instances, the exemplary imaging system 10 may include or may be in communication with one or more sensor-based motion measurement systems 34. The sensor-based motion measurement systems 34 typically comprise one or more sensors 36 in the form of a pad or contact that may be disposed on skin surface of the patient 14. The contact area of a sensor 36 may vary in size from micrometers to centimeters in diameter and height. The size selected is usually based on an application. Similarly, the number of sensors 36 used may depend on the application.

When disposed on the patient 14, the sensor 36 may detect and/or measure some metric or parameter of interest, such as a mechanical event, that may be used as an indicator of internal motion. The sensor 36 may be connected to the respective sensor-based measurement system 34 via one or more leads 38 which may transmit a signal representative of the sensed metric or parameter to the respective system 34 for processing. In some contexts, the sensor 36 may communicate with the respective sensor-based motion detection system 34 via wireless means, such as a wireless network protocol, as opposed to a physical lead 38.

Sensor-based systems 34 may measure mechanical or physical activity to determine respiratory motion. For example, internal movement caused by respiration may create mechanical motion detectable by one or more suitable sensors 36 disposed on the skin of the patient 14 as pressure, displacement, acceleration, velocity, pressure, and/or other mechanical indicators of motion. In this manner, internal motion of one or more respiratory organs may be detected and/or measured by various types sensors 36, including accelerometers, optical markers, displacement sensors, force sensors, ultrasonic sensors, strain gauges, photodiodes, and pressure sensors.

As depicted in FIG. 1, one or more sensors 36 may be employed. In particular, at least one sensor may be deployed along each perpendicular axis of motion for which motion data is to be collected via the sensor-based motion detection system 34. For example, in FIG. 1, an x-axis sensor 40 is situated on a sagittal plane relative to the patient 14, i.e., on the side of the thorax of the patient 14. In this configuration, the x-axis sensor 40 may measure internal motion along the x-axis. Similarly, a y-axis sensor 42 may be situated on a coronal plane relative to the patient 14, i.e., on the front abdominal wall of the patient 14. In this configuration, the y-axis sensor 42 may measure internal motion along the y-axis. The location of the sensors 36 may be adjusted based on whether patient 14 is a "belly breather" or "chest breather."

While only a single x-axis sensor 40 and y-axis sensor 42 are depicted in FIG. 1, more than one sensor 36 may be situated along an axis of interest. If more than one sensor 36 is situated along an axis, the sensors 36 may be arranged in an array or matrix. Typically, sensors 36 arranged in an array or matrix are spaced equidistant from each other.

The exemplary system depicted in FIG. 1 depicts a generic imaging modality that may be used in accordance with the present technique. To facilitate the description of the present technique, however, the following examples will be presented in the context of a specific imaging modality, namely MRI. An one of ordinary skill in the art will appreciate, however, the present technique may be applied to a variety of imaging modalities, such as CT, PET, and so forth, and is not limited to the MRI modality.

Figure 2:
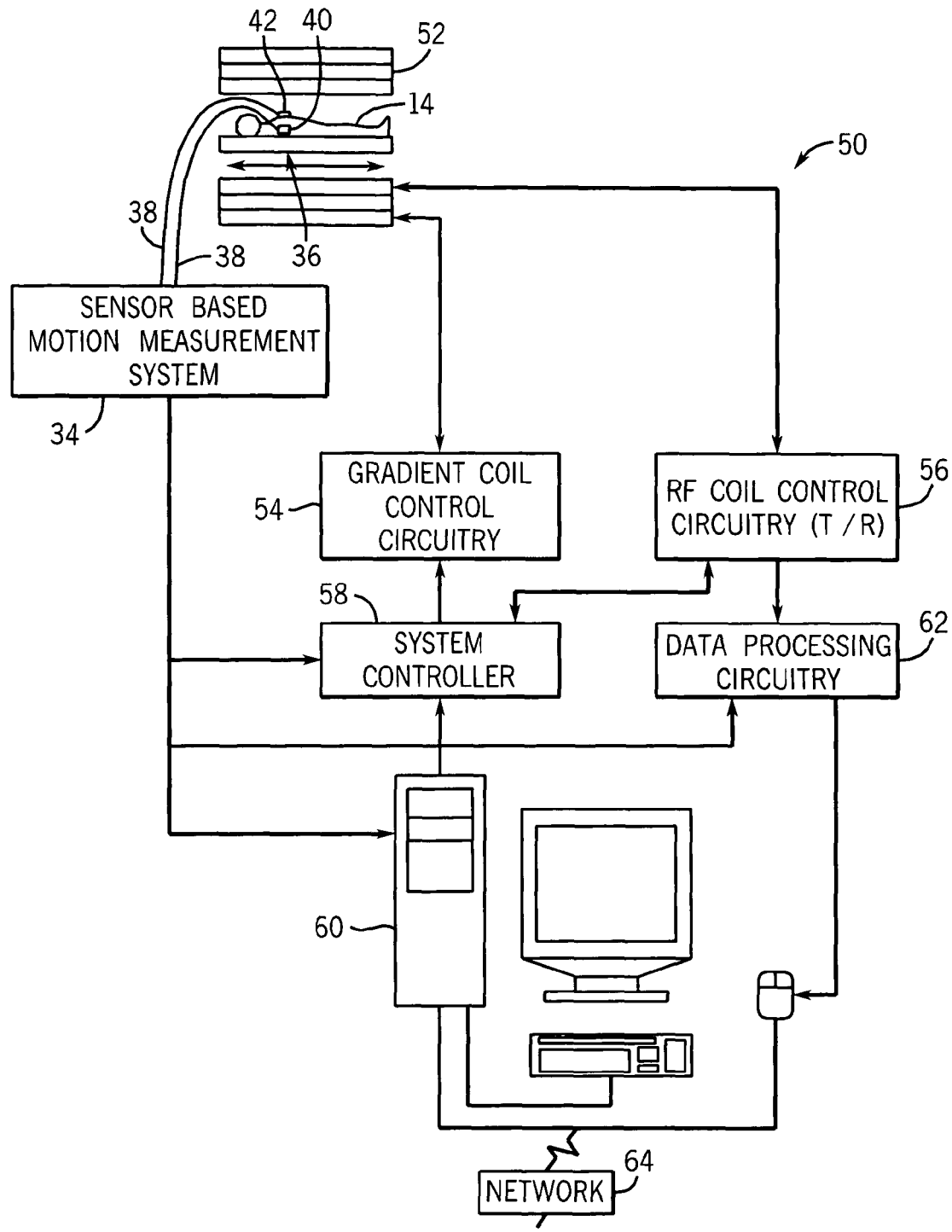
FIG. 2 is a diagrammatical representation of an exemplary magnetic resonance imaging system which may be employed in the technique.

Referring now to FIG. 2, an exemplary MRI system 50 is depicted. The system 50 includes a scanner 52 in which a patient 14 is positioned for acquisition of image data. The scanner 52 generally includes a primary magnet for generating a magnetic field that influences gyromagnetic materials within the patient's body. As the gyromagnetic material, typically water and metabolites, attempts to align with the magnetic field, gradient coils produce additional magnetic fields that are orthogonally oriented with respect to one another. The gradient fields effectively select a slice of tissue through the patient 14 for imaging, and encode the gyromagnetic materials within the slice in accordance with phase and frequency of their rotation. A radio-frequency (RF) coil in the scanner 52 generates high frequency pulses to excite the gyromagnetic material and, as the material attempts to realign itself with the magnetic fields, magnetic resonance signals are emitted which are collected by the radio-frequency coil.

The scanner 52 is coupled to gradient coil control circuitry 54 and to RF coil control circuitry 56. The gradient coil control circuitry 54 permits regulation of various pulse sequences that define imaging or examination methodologies used to generate the image data. Pulse sequence descriptions implemented via the gradient coil control circuitry 54 are designed to image specific slices, anatomies, as well as to permit specific imaging of moving tissue, such as blood, and defusing materials. The pulse sequences may allow for imaging of multiple slices sequentially, such as for analysis of various organs or features, as well as for three-dimensional image reconstruction. The RF coil control circuitry 56 permits application of pulses to the RF excitation coil, and serves to receive and partially process the resulting detected MR signals. It should also be noted that a range of RF coil structures may be employed for specific anatomies and purposes. In addition, a single RF coil may be used for transmission of the RF pulses, with a different coil serving to receive the resulting signals.

The gradient and RF coil control circuitry 54, 56 function under the direction of a system controller 58. The system controller 58 implements pulse sequence descriptions that define the image data acquisition process. The system controller 58 will generally permit some amount of adaptation or configuration of the examination sequence by means of an operator interface 60.

Data processing circuitry 62 receives the detected MR signals and processes the signals to obtain data for reconstruction. In general, the data processing circuitry 62 digitizes the received signals, and performs a two-dimensional fast Fourier transform on the signals to decode specific locations in the selected slice from which the MR signals originated. The resulting information provides an indication of the intensity of MR signals originating at various locations or volume elements (voxels) in the slice. Each voxel may then be converted to a pixel intensity in image data for reconstruction. The data processing circuitry 62 may perform a wide range of other functions, such as for image enhancement, dynamic range adjustment, intensity adjustments, smoothing, sharpening, and so forth. The resulting processed image data is typically forwarded to the operator interface 60 for viewing, as well as to short or long-term storage. As in the case of foregoing imaging systems, MR image data may be viewed locally at a scanner location, or may be transmitted to remote locations both within an institution and remote from an institution such as via a network connection 64.

In addition, a sensor-based motion measurement system 34 may be present which acquires motion data perpendicular to the body of patient 14 via one or more sensors 36. In particular, sensor-based motion measurement is useful for determining one-dimensional motion continuously over time. As depicted, the sensors 36 may include an x-axis sensor 40 situated on the side of the patient 14 and/or a y-axis sensor 42 disposed on the patient's chest. The sensors 36 may transmit the measured motion data to the sensor-based motion measurement system 34 as electrical signals, either via leads 38 or by wireless means. The sensor-based motion measurement system 34 may process the acquired signals to estimate the motion of an organ along the measured axes or may transmit the raw motion data to other processor-based components of the MRI system 50 for motion estimation or determination. For example, the sensor-based motion measurement system 34 may provide the raw or processed motion data to the system controller 58, the data processing circuitry 62, and/or the operator workstation 60 for motion estimation or subsequent operations.

In addition to the sensor-based motion determination techniques discussed above, motion determination for the organ or organs of interest may be performed using data obtained from the imaging system itself. These data-based techniques include pre-acquisition imaging techniques, such as Navigator pulses in MR systems, scout images in CT systems or fluoroscopic images in other generalized X-ray applications, may be employed to determine the motion of the lungs, diaphragm, chest wall, and so forth. Pre-acquisition motion measurement typically involves determining the position of the organ or organs of interest by a pre-acquisition measurement using the imaging system 10. The motion of the organ or organs may then be subsequently determined based upon the pre-acquisition reference point.

For example, in MRI, the Navigator echo method may use a non-phase-encoded readout of the current imaging slice, a two-dimensional pencil beam, or a full three-dimensional acquisition to measure the position the diaphragm or some other anatomical landmark before collecting imaging data. A narrow area perpendicular to the movement of the organ of interest may be imaged where the contrast of a moving interface is typically high. For example, where a two-dimensional pencil beam sequence is employed, the signal from a narrow volume perpendicular to the moving structure is acquired, such as a vertical volume in the superior/inferior direction for the diaphragm. The high-contrast moving interface may be used to automatically detect motion of the object, such as the diaphragm. Hence, the Navigator echo technique may be used as a motion determination technique that does not utilize additional sensing equipment, as the MR system itself provides the sensing. Other methods, such as orbital or spherical Navigator techniques, may be used to detect the motion of a rigid body in more than one dimension, however, these methods are generally not reliable for estimating the motion of non-rigid structures, In addition, data-based techniques may derive motion data from the acquisition image data, prior or subsequent to reconstruction, i.e., from the acquired and/or reconstructed image domains. For example, a slab of data may be acquired in the torso region, such as in the region of the lungs or diaphragm. The image data may be acquired as part of two-dimensional or three-dimensional images. In the example of the diaphragm, one method of determining motion in the acquired image data is to track a pre-defined coverage area in the z-direction near the diaphragm over time.

Segmentation techniques may be used to differentiate the diaphragm from other abdominal organs. A variety of segmentation techniques or combinations of techniques may be used, including, but not limited to, iterative thresholding, k-means segmentation, edge detection, edge linking, curve fitting, curve smoothing, 2D/3D morphological filtering, region growing, fuzzy clustering, image/volume measurements, heuristics, knowledge-based rules, decision trees, neural networks, and so forth.

Segmentation may be performed manually and/or automatically. For example, manual segmentation may involve displaying the data, such as at the operator workstation 60, and allowing a user to delineate the region using an input device, such as a mouse, keyboard, touch screen, and so forth. Automated segmentation may be performed by algorithms that utilize prior knowledge, such as the shape and size of the organ of interest, such as the diaphragm. Combinations of manual and automatic segmentation, i.e., semi-automated processes, may also be employed, such as where automated routines are used to preliminarily segment the data and operator input is used to confirm or revise the segmentation. After segmentation, regions of interest within the segmented structures may be used to determine the motion over time at the regions.

Using acquired image data to determine motion in this manner, a two-dimensional coronal data set or image may be used to determine frontal plane motion. Similarly, a two-dimensional sagittal data set may be used to determine sagittal plane motion and a two-dimensional axial data set may be used to determine horizontal plane motion. In this manner, three-dimensional motion, such as respiratory motion, may be derived using acquired and/or reconstructed image data.

In these manners, useful three-dimensional motion estimation for an organ, such as the lungs or diaphragm, may be accomplished using one or more of the sensor and data-based motion determination techniques discussed above. For example, referring to FIG. 3, a generic example is provided for the estimation of three-dimensional motion of an organ. As depicted in the example, x-axis motion data 70 may be acquired at step 72 from a source of x-axis motion data 74. The source 74 may be one or more sensors 36 or an image data acquired form an imager 12, in accordance with the sensor-based and data-based techniques previously discussed. Similarly, y-axis motion data 76 and z-axis motion data 78 may be similarly acquired at respective steps 80 and 82 from respective y-axis motion data sources 84 and z-axis motion data sources 86. The respective motion data sources 74, 84, 86 may be identical, such as image data acquired from an imager 12 or sensors 36 suitably disposed to measure motion for each axis. Alternatively, the motion data sources 74, 84, 86 may be some combination of sensor-data and image-data based sources such that sensor-based sources may comprise the source of motion data for one axis while image-data based sources may comprise the source of motion data for another axis. In this way the best-suited or most readily available source for measuring motion data along each axis may be employed.

It is worth noting that the type of source may vary even within sensor-based and image-data based source categories. For example, sensors 36 may be used as a source of motion data for two different axes, however, one type of sensors may be employed on one axis, such as accelerometers, and a second type of sensor may be employed at the second axis, such as pressure sensors. Similarly, image-data may be used as a source of motion data for more than one axis, however different data-based techniques may be employed in measuring motion data along the different axes. For example, pre-acquisition image data may be the source of motion data along one axis while an acquisition image data, from either the raw or reconstructed image domain, may be the source of motion data along a different axis. Therefore, the respective motion data sources 74, 84, 86 may include the most suitable and/or convenient combination of sources available.

Once the x-axis motion data 70, y-axis motion data 76, and z-axis motion data 78 are acquired, the concurrent motion vectors associated with the x-axis, y-axis, and z-axis motion, as determined form the respective motion data sets 70, 76, and 78, may be combined at step 88 to generate a set of three-dimensional motion data 90 for the organ of interest which is continuous over time. The three-dimensional motion data 90 derived by technique of FIG. 3 may be obtained in substantially real-time where suitable motion data sources are available such as motion data obtained from sensors and/or from data-based techniques based on pre-acquisition image data. In such cases, the three-dimensional motion data may be used prospectively, such as for gating of the acquisition process and so forth. Alternatively, the three-dimensional motion data may be generated and used in a retrospective manner, such as for retrospective gating in instances where the motion data sources are better suited for retrospective uses. For example, data based techniques based on acquisition image data, either in the raw or reconstructed domains, may be better suited for retrospective applications.

Once derived, the three-dimensional motion data 90 of the lungs, diaphragm, or other organ of interest may be used to track pathologies, such as tumors, over time. For example, the three-dimensional motion data 90 may be used for gating, radiation therapy planning, surgical planning, surgical navigation, and follow-up diagnosis. In addition, the three-dimensional motion data 90 obtained via the present technique may be used to generate motion correction factors to offset or correct for patient motion during imaging, allowing motion artifacts to be reduced or eliminated from the reconstructed images.

Figure 3:
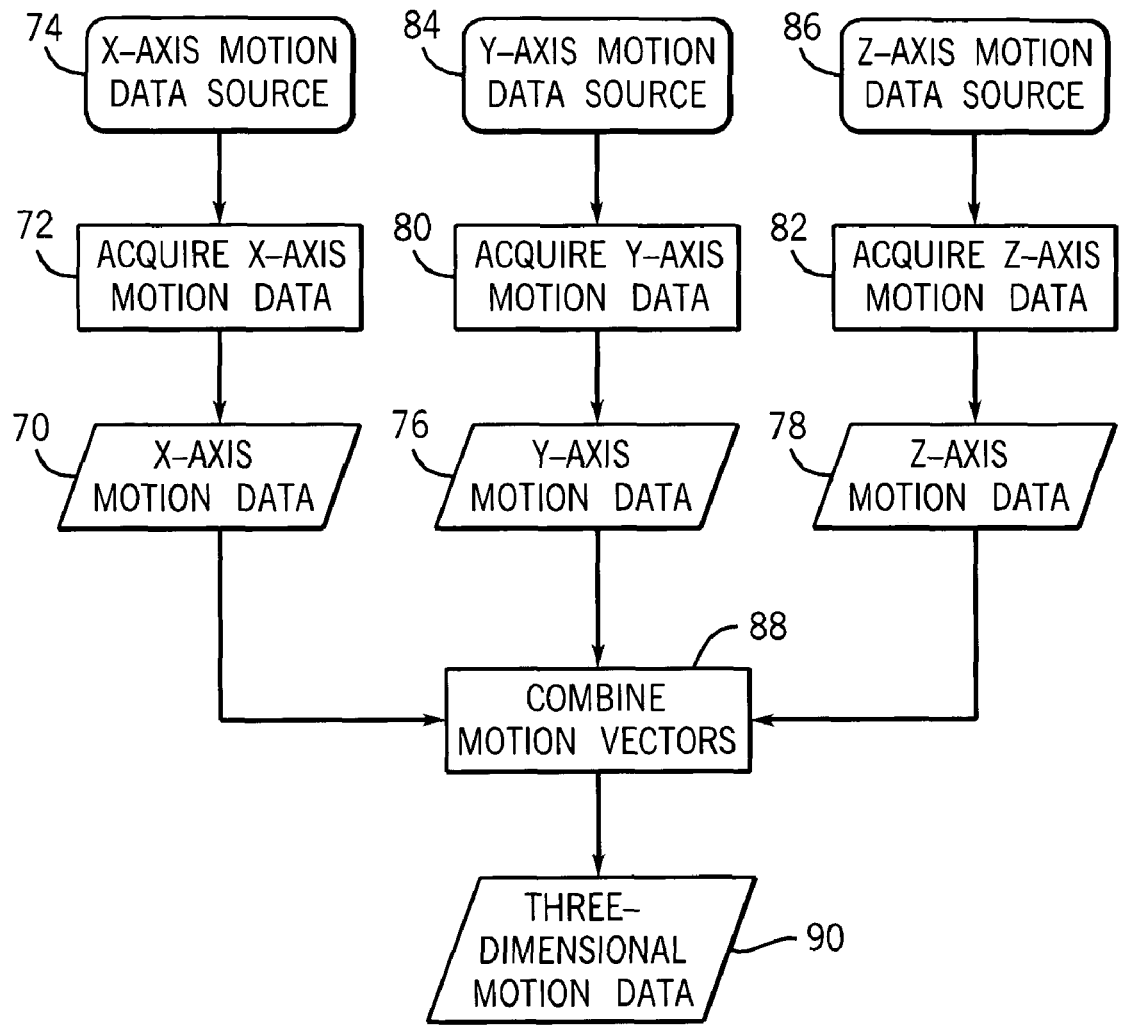
FIG. 3 is a flowchart depicting the determination of three-dimensional motion, in accordance with the present technique.
Figure 4:
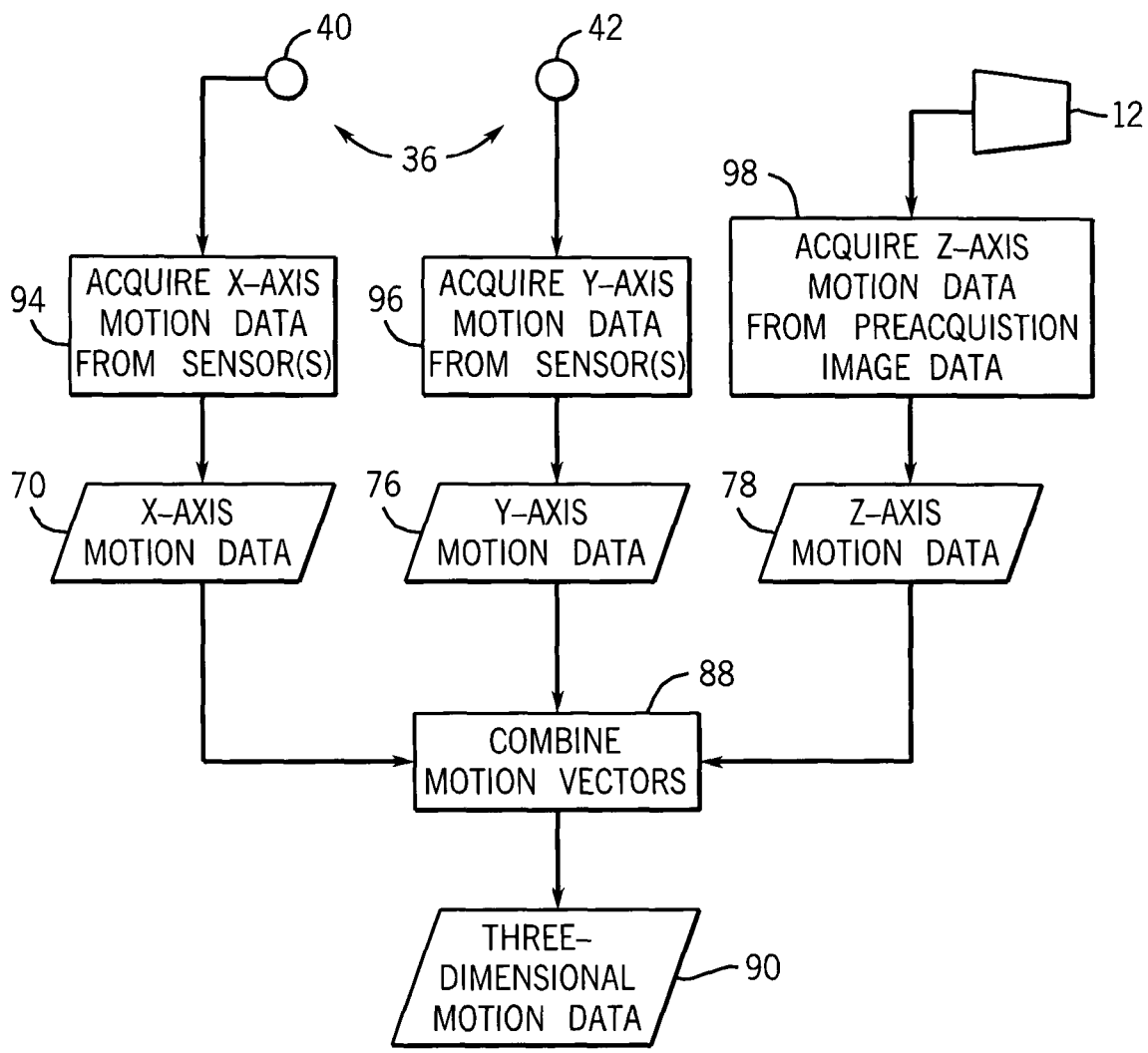
FIG. 4 is a flowchart depicting the determination of three-dimensional motion using both sensor-based and data-based methodologies, in accordance with the present technique.

A specific example of the technique as described in FIG. 3, utilizing both sensor-based and data-based motion estimation, is provided in FIG. 4. As depicted in FIG. 4, organ motion in the xy-plane may be continuously acquired by sensors 36 such that x-axis motion data 70 is acquired from the x-axis sensor 40 at step 94 and y-axis motion data 76 is acquired from the y-axis sensor 42 at step 96. Conversely, the z-axis motion data 78 may be acquired at step 98 from pre-acquisition image data acquired from the imager 12. For example, an MR scanner utilizing a Navigator echo or other pre-acquisition motion measurement technique may be used to acquire the z-axis motion data 78 at step 98. The concurrent motion vectors associated with the x-axis, y-axis, and z-axis motion data 70, 76, and 78 may be combined at step 88 to generate a set of three-dimensional motion data 90 for the organ of interest which is continuous over time. The three-dimensional motion data 90 derived by the technique of FIG. 4 may be obtained in substantially real-time and, in addition, may be used prospectively, such as for gating of the acquisition process and so forth.

Figure 5:
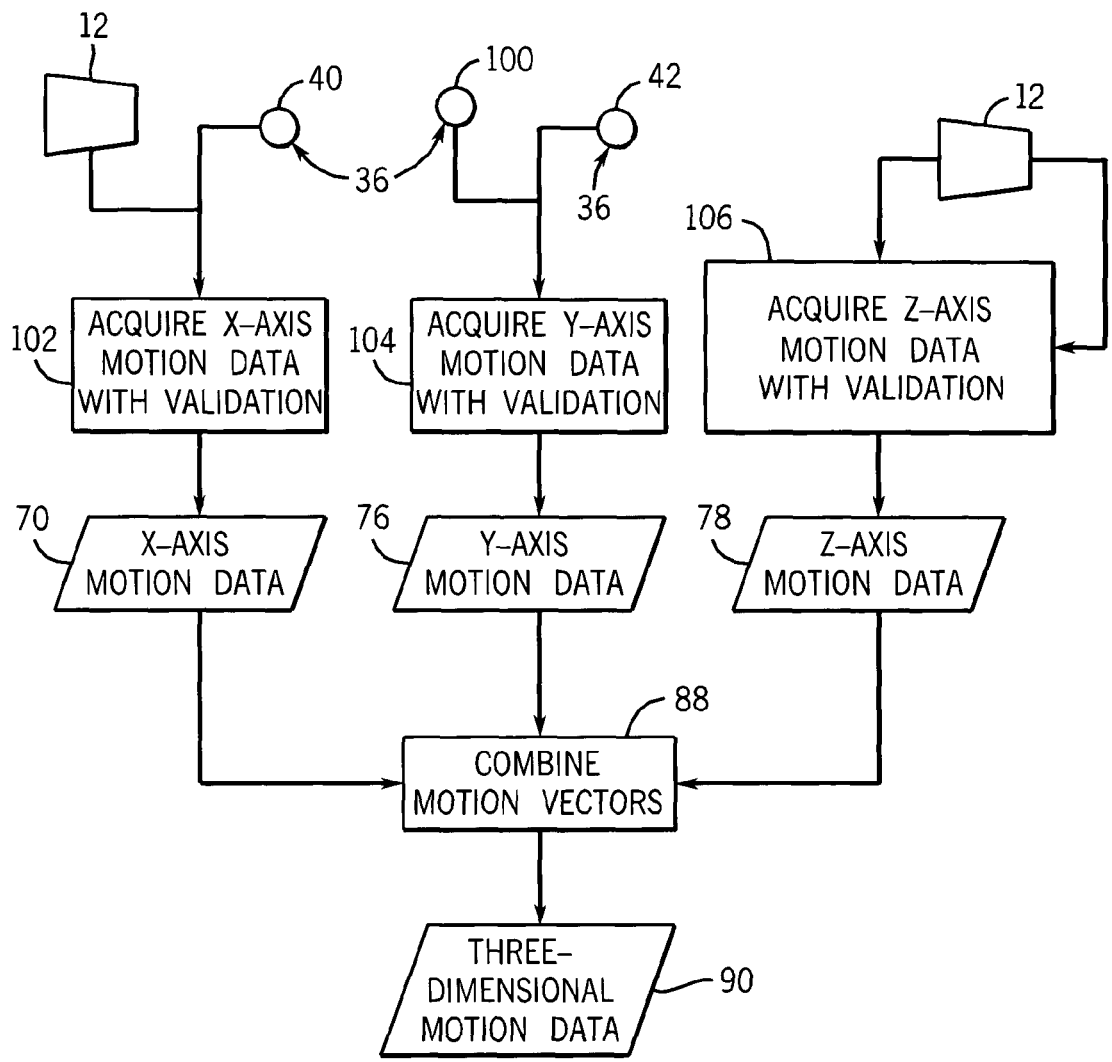
FIG. 5 is a flowchart depicting the determination of three-dimensional motion with validation, in accordance with the present technique.

As depicted in FIG. 5, the motion estimates 70, 74, 78 may be validated where one or more additional sources of motion data are available. For example, motion data acquired for an axis from a sensor 36, here x-axis sensor 40, may be validated against motion data acquired for the axis using data-based techniques, such as from pre-acquisition image data or acquisition image data. Similarly, motion data acquired for an axis from a sensor 36, such as y-axis sensor 42, may be validated against motion data acquired for the axis using a validation sensor 100 which may measure the same parameter as y-axis sensor 42 or a different parameter. Similarly, motion data acquired for an axis using a first data-based technique, such as from pre-acquisition image data, may be validated against motion data acquired from the axis using a different data-based technique, such a data based-technique which determines motion from raw or reconstructed acquisition image data.

For example, a metric of reliability of motion correlation between the two sources of motion data for an axis may be established, such as over numerous studies. A fraction of that metric may then be used as a reliability threshold. The reliability threshold and the acquired motion data from the two sources may be used to validate the acquired motion data, as depicted at acquisition step 102 for the x-axis, acquisition step 104 for the y-axis, and acquisition step 106 for the z-axis. The validation may occur concurrent with or subsequent to acquisition of the motion data, as desired or based upon the availability of the validating motion data. As one of ordinary skill in the art will appreciate, phase variations between the sensor-based and image-based motion data may be accounted for during the validation process as needed. If the second source of motion data validates the first source, such as based upon the reliability criterion discussed above, the motion data may be derived and used as described above. If the second source of motion data fails to validate the first source, a variety of response may be triggered, such as notification of an operator, termination of the measurement process, or continuation of the motion data acquisition process using either the first or second source of motion data without validation. The motion data 70, 76, 78 may be used to generate concurrent motion vectors for combination at step 88 to generate the three-dimensional motion data 90. While the preceding discussion describes the use of two sources of motion data along an axis for acquisition and validation, one of ordinary skill in the art will readily apprehend that more than two sources may be available and employed for acquisition and validation of motion data along an axis.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for determining the motion of an organ, comprising the steps of:
   acquiring a first set of one-dimensional motion data for an organ along a first axis by a first methodology;
   acquiring a second set of one-dimensional motion data for the organ along a second axis by a second methodology, wherein the first axis and the second axis are perpendicular;
   acquiring a third set of one-dimensional motion data for the organ along a third axis by a third methodology, wherein the third axis is perpendicular to the first axis and the second axis;
   deriving one or more concurrent motion vectors from each of the first, second, and third sets of one-dimensional motion data; and
   combining the one or more concurrent motion vectors to generate a set of three-dimensional motion data for the organ.

2. The method as recited in claim 1, wherein:
   acquiring at least one set of one-dimensional motion data comprises measuring the motion along the one or more respective axes with a set of one or more sensors.

3. The method as recited in claim 1, wherein:
   acquiring at least one of the first, second, or third set of one-dimensional motion data comprises validating the one or more sets of one-dimensional motion data using one or more respective sets of validation motion data.

4. The method as recited in claim 1, wherein
   acquiring at least one set of one-dimensional motion data comprises determining the motion along the one or more respective axes from a respective set of motion data derived from an imager.

5. The method as recited in claim 4, wherein the respective set of motion data is derived from a set of acquisition image data or pre-acquisition image data.

6. The method as recited in claim 5, wherein the set of acquisition image data comprises a set of unreconstructed image data or a set of reconstructed image data.

7. The method as recited in claim 1, wherein two of the first methodology, the second methodology or the third methodology comprise the same methodology.

8. The method as recited in claim 1, wherein at least one of the first methodology, the second methodology or the third methodology comprises a sensor-based methodology, and wherein at least one of the first methodology, the second methodology or the third methodology comprises an image-based methodology.

9. The method as recited in claim 1, wherein the first methodology, the second methodology or the third methodology comprise one or more data-based methodologies, wherein the one or more data-based methodologies determine motion from one or more respective sets of acquisition image data.

10. The method as recited in claim 9, wherein the one or more respective sets of acquisition image data comprise one or more sets of unreconstructed image data.

11. The method as recited in claim 9, wherein the one or more respective sets of acquisition image data comprise one or more sets of reconstructed image data.

12. A—non-transitory—computer readable storage medium having executable code stored thereon, the executable code comprising:
   a routine for acquiring a first set of one-dimensional motion data for an organ along a first axis by a first methodology;
   a routine for acquiring a second set of one-dimensional motion data for the organ along a second axis by a second methodology, wherein the first axis and the second axis are perpendicular;
   a routine for acquiring a third set of one-dimensional motion data for the organ along a third axis by a third methodology, wherein the third axis is perpendicular to the first axis and the second axis;

a routine for deriving one or more concurrent motion vectors from each of the first, second, and third sets of one-dimensional motion data; and a routine for combining the one or more concurrent motion vectors to generate a set of three-dimensional motion data for the organ.

13. The computer readable storage medium, as recited in claim 12, wherein:

at least one routine for acquiring at least one of the first, second, or third set of one-dimensional motion data acquires the one-dimensional motion data along the one or more respective axes from a set of one or more sensors.

14. The computer readable storage medium as recited in claim 12, wherein:

at least one routine for acquiring at least one of the first, second, or third set of one-dimensional motion data validates the one or more sets of one-dimensional motion data using one or more respective sets of validation motion data.

15. The computer readable storage medium as recited in claim 12, wherein:

at least one routine for acquiring at least one of the first, second, or third set of one-dimensional motion data determines the one-dimensional motion along the one or more respective axes from a respective set of motion data derived from an imager.

16. The computer readable storage medium, as recited in claim 15, wherein the respective set of motion data is derived from a set of acquisition image data or a set of pre-acquisition image data.

17. The computer readable storage medium, as recited in claim 16, wherein the set of acquisition image data comprises a set of unreconstructed image data or a set of reconstructed image data.

18. The computer readable storage medium, as recited in claim 12, wherein two of the first methodology, the second methodology or the third methodology comprise the same methodology.

19. The computer readable storage medium, as recited in claim 12, wherein at least one of the first methodology, the second methodology or the third methodology comprises a sensor-based methodology, and wherein at least one of the first methodology, the second methodology or the third methodology comprises an image-based methodology.

20. The computer readable storage medium, as recited in claim 12, wherein the first methodology, the second methodology or the third methodology comprise one or more data-based methodologies, wherein the one or more data-based methodologies determine motion from one or more respective sets of acquisition image data.

21. The computer readable storage medium, as recited in claim 20, wherein the one or more respective sets of acquisition image data comprise one or more sets of unreconstructed image data.

22. The computer readable storage medium, as recited in claim 20, wherein the one or more respective sets of acquisition image data comprise one or more sets of reconstructed image data.

23. An imaging system, comprising, an imager configured to generate a plurality of signals representative of one or more structures within a region of interest;

a sensor-based motion determination system configured to acquire one-dimensional motion data from one or more sensors;

data acquisition circuitry configured to acquire the plurality of signals;

data processing circuitry configured to process the plurality of signals;

system control circuitry configured to operate at least one of the imager or the data acquisition circuitry; and an operator workstation configured to communicate with the system control circuitry and to receive the processed plurality of signals from the data processing circuitry;

wherein the imager, the sensor-based motion determination system, or a combination of the imager and the sensor-based motion determination system is configured to acquire a first, a second, and a third set of one-dimensional motion data for an organ along respective first, second, and third perpendicular axes; and wherein at least one of the sensor-based motion determination system, the data processing circuitry, or the operator workstation are configured to derive one or more concurrent motion vectors from each of the first, second, and third sets of one-dimensional motion data and to combine the one or more concurrent motion vectors to generate a set of three-dimensional motion data for the organ.

24. The imaging system, as recited in claim 23, wherein at least one of the sensor-based motion determination system, the data processing circuitry, or the operator workstation is configured to validate one or more sets of one-dimensional motion data using one or more respective sets of validation motion data.

25. The imaging system, as recited in claim 23, wherein the one or more sensors comprise at least one of an accelerometer, an optical marker, a displacement sensor, a force sensor, an ultrasonic sensors, a strain gauge, a photodiode, or a pressure sensor.

26. The imaging system, as recited in claim 23, wherein at least one of the first, the second, or the third set of one-dimensional motion data is determined from a respective set of motion data acquired by the imager.

27. The imaging system, as recited in claim 26, wherein the respective set of motion data is a set of pre-acquisition image data or a set of acquisition image data.

28. The imaging system, as recited in claim 27, wherein the set of acquisition image data comprises a set of unreconstructed image data- or a set of reconstructed image data.

29. The imaging system, as recited in claim 23, wherein the first and second sets of one-dimensional motion data are acquired by the sensor-based motion determination system.

30. The imaging system, as recited in claim 23, wherein the first, second, and third sets of one-dimensional motion data are acquired by the sensor-based motion determination system.

31. An imaging system, comprising, an imager configured to generate a plurality of signals representative of one or more structures within a region of interest and to acquire at least one set of acquisition image data used to derive a first, a second, and/or a third set of one-dimensional motion data for an organ along respective first, second, and third perpendicular axes;

data acquisition circuitry configured to acquire the plurality of signals;

data processing circuitry configured to process the plurality of signals;

system control circuitry configured to operate at least one of the imager or the data acquisition circuitry; and an operator workstation configured to communicate with the system control circuitry and to receive the processed plurality of signals from the data processing circuitry; and wherein at least one of the data processing circuitry or the operator workstation is configured to derive one or more concurrent motion vectors from each of the first, second, and third sets of one-dimensional motion data and to combine the one or more concurrent motion vectors to generate a set of three-dimensional motion data for the organ.

32. The imaging system, as recited in claim 31, wherein the at least one set of acquisition data comprises one or more sets of unreconstructed image data.

33. The imaging system, as recited in claim 31, wherein the at least one set of acquisition data comprises one or more sets of reconstructed image data.

34. The imaging system, as recited in claim 31, wherein at least one of the data processing circuitry or the operator workstation is configured to validate one or more sets of one-dimensional motion data using one or more respective sets of validation motion data.

35. The method as recited in claim 1, wherein at least one of the first, second, or third sets of one-dimensional motion data comprises measured mechanical motion data for the organ.

36. The method as recited in claim 2, wherein the one or more sensors are affixed to a subject of interest.

37. The computer readable storage medium, as recited in claim 12, wherein at least one of the first, second, or third sets of one-dimensional motion data comprises measured mechanical motion data for the organ.

38. The computer readable storage medium, as recited in claim 13, wherein the one or more sensors are affixed to a subject of interest.

39. The imaging system, as recited in claim 23, wherein at least one of the first, second, or third sets of one-dimensional motion data is acquired by the imager, and wherein at least one of the first, second, or third sets of one-dimensional motion data is acquired by the sensor-based motion determination system.

40. The imaging system, as recited in claim 23, wherein the one or more sensors are affixed to a subject of interest such that the one or more sensors is stationary with respect to the subject of interest.

41. The imaging system, as recited in claim 23, wherein at least one of the first, second, or third sets of one-dimensional motion data comprises measured mechanical motion data for the organ.

42. An imaging system, comprising, an imager configured to generate a plurality of signals representative of one or more structures within a region of interest of a patient;

a sensor-based motion determination system configured to acquire one-dimensional motion data from one or more sensors, wherein at least one of the one or more sensors comprises a pad configured to affix the sensor to a body surface of the patient;

data acquisition circuitry configured to acquire the plurality of signals;

data processing circuitry configured to process the plurality of signals;

system control circuitry configured to operate at least one of the imager or the data acquisition circuitry; and an operator workstation configured to communicate with the system control circuitry and to receive the processed plurality of signals from the data processing circuitry;

wherein the imager, the sensor-based motion determination system, or a combination of the imager and the sensor-based motion determination system is configured to acquire a first, a second, and a third set of one-dimensional motion data for an organ along respective first, second, and third perpendicular axes;

wherein at least one of the sensor-based motion determination system, the data processing circuitry, or the operator workstation are configured to derive one or more concurrent motion vectors from each of the first, second, and third sets of one-dimensional motion data and to combine the one or more concurrent motion vectors to generate a set of three-dimensional motion data for the organ; and wherein the one or more sensors are configured to remain generally stationary with respect to the position of the patient during the acquisition of the first, second, and third sets of one dimensional motion data.

* * * * *